United States Patent [19]

Vale, Jr. et al.

[11] Patent Number: 4,973,577
[45] Date of Patent: Nov. 27, 1990

[54] FSH-RELEASING PEPTIDES

[75] Inventors: Wylie W. Vale, Jr.; Jean E. F. Rivier, both of La Jolla; Richard A. McClintock, San Diego; Anne Corrigan, San Diego; Joan Vaughan, San Diego; Joachim Spiess, Encinitas; Nicholas C. Ling; Shao-Yao Ying, both of San Diego; Frederick S. Esch, Foster City; Roger C. L. Guillemin, La Jolla, all of Calif.

[73] Assignee: The Salk Institute for Biological Studies, San Diego, Calif.

[21] Appl. No.: 91,696

[22] Filed: Aug. 31, 1987

Related U.S. Application Data

[63] Continuation-in-part of Ser. No. 848,363, Apr. 4, 1986, abandoned, and a continuation-in-part of Ser. No. 849,108, Apr. 7, 1986, abandoned.

[51] Int. Cl.$^5$ .......................... A61K 37/24; C07K 7/10; C07K 7/20
[52] U.S. Cl. .......................... 514/12; 514/2; 514/21; 514/800; 530/313; 530/399
[58] Field of Search ............... 514/2, 12, 21; 530/313, 530/399

[56] References Cited

U.S. PATENT DOCUMENTS

| | | | |
|---|---|---|---|
| 4,409,139 | 10/1983 | Ling et al. | 530/313 |
| 4,734,398 | 3/1988 | diZerega | 514/2 |
| 4,764,502 | 8/1988 | diZerega | 514/2 |
| 4,798,885 | 1/1989 | Mason | 530/300 |

FOREIGN PATENT DOCUMENTS

0210461A2  4/1987  European Pat. Off. .
0222491    5/1987  European Pat. Off. .

OTHER PUBLICATIONS

Goodman and Gilman, *The Pharmaceutical Basis of Therapeutics*, 3rd. ed., The MacMillan Co., N.Y., 1965, pp. 1527–1531.
Proc. Nat'l. Acad. Sci., 82, pp. 7217–7221, (1985).
Biochem. and Biophys. Res. Commun., 133, (1985), 120–127.
Brain, Res. Bull., vol. 10, (1983), 623–629.

*Primary Examiner*—F. T. Moezie
*Attorney, Agent, or Firm*—Fitch, Even, Tabin & Flannery

[57] ABSTRACT

A 28,000-dalton protein with FSH-releasing activity is isolated from porcine follicular fluid in a multi-step procedure including gel filtration, ion exchange chromatography and several reverse-phase high-performance liquid chromatography steps. The 28 kD protein promotes secretion of FSH, but not of LH, in a rat anterior pituitary monolayer culture system, exhibiting an $EC_{50}$ of 0.5 ng/ml. These peptides are dimers of inhibin $\beta$-chains of mammals, and homodimers or heterodimers of the $\beta_A$ and $\beta_B$ chains are biologically active to regulate fertility of various mammalian species, including humans.

19 Claims, 5 Drawing Sheets

```
βA Subunit        10                    20                30
 G L E C D G K V N I C C K K Q F F V S F K D I G W N D W I I
 G L E C D G R T N L C C R Q Q F F I D F R L I G W S D W I I
βB Subunit
                         40                50                        60
 A P S G Y H A N Y C E G E C P S H I A G T S G S S L S F H S
 A P T G Y Y G N Y C E G S C P A Y L A G V P G S A S S F H T 70                80                        90
 T V I N H Y R M R G H S P F A N L K S C C V P T K L R P M S
 A V V N Q Y R M R G L N P   G T V N S C C I P T K L S T M S 100               110
 M L Y Y D D G Q N I I K K D I Q N M I V E E C G C S
 M L Y F D D E Y N I V K R D V P N M I V E E C G C A
```

FIG.4b

FSH-RELEASING PEPTIDES

This invention was made with Government support under Grants HD-13527, AM-26741, HD-09690 and AM-18811 of the National Institutes of Health (DHHS) and under Contract NO1-HD-32826 of NICHD. The Government has certain rights in this invention.

This application is a continuation-in-part of applications Ser. No. 848,363, filed Apr. 4, 1986, now abandoned and Ser. No. 849,108, filed Apr. 7, 1986, now abandoned.

The present invention relates to peptides which affect the release of hormones from the pituitary and more particularly to a protein which promotes the release of follicle-stimulating hormone from the anterior lobe of the pituitary gland.

BACKGROUND OF THE INVENTION

There has been considerable interest in hormones which affect the release of hormones from the anterior lobe of the pituitary gland, in particular luteinizing hormone (LH) and follicle-stimulating hormone (FSH). A variety of hypophysiotropic peptides or proteins have been reported to be present in mammalian gonads. Gonadotropin releasing hormone (GnRH), a decapeptide, which is also known as luteinizing hormone release factor (LRF) is a peptide found to stimulate the release of both LH and FSH. Proteins termed "inhibins", which selectively suppress the secretion of FSH but, under most circumstances, do not suppress the release of LH, have been recently isolated and characterized from gonadal fluids of several species, Robertson et al., *Biochem. Biophys. Res. Commun.* 126, 220–226 (1985); Miyamoto et al., *Biochem. Biophys. Res. Commun.* 129, 396–503 (1985); Rivier et al., *Biochem. Biophys. Res. Commun.* 133, 120–127 (1985); Ling et al., *P.N.A.S.* 82, 7217–7221 (1985). Mason et al., *Nature*, 318, 659–663 (1985) disclosed the complete amino acid sequences of porcine inhibin α subunit and two distinct β subunits, $\beta_A$ and $\beta_B$. Gonadotropin-releasing peptides have also been described in the gonads which have generally been shown to have activity in radioreceptor assays for GnRH but to exhibit different chromatographic and immunologic characteristics from that of GnRH, Igarashi et al. *Endocrinology* 74: 446–452 (1964); Igarashi et al., In *Psychoncuroendocrinology*, ed. by Hatotani et al., pp. 178–186 (1973); Lundanes et al., *Biochem. Biophys. Res. Commun.* 94: 827–836 (1980) and Samson et al., *Peptides* 1:97–102 (1980).

Described herein are proteins which are found in mammalian follicular fluid and which have action opposite that of inhibin, stimulating the release of FSH from the pituitary but not stimulating the release of LH. Such a peptide is generally referred to herein as "FSH-releasing peptide" (FRP) but is sometimes also referred to as "activin".

SUMMARY OF THE INVENTION

A protein having a molecular weight of about 28,000 daltons (28 kD) and having FSH-releasing activity has been successfully isolated to substantial homogeneity from porcine follicular fluid(pFF). The 28 kD protein exhibits FRP activity in that it specifically stimulates the secretion and synthesis of FSH by cultured rat anterior pituitary cells but does not stimulate release of LH or other known pituitary hormones.

The protein has a molecular weight of about 28 kD as determined by sodium dodecyl sulfate-polyacrylamide gel electrophoresis (SDS-PAGE); under reducing conditions, a major band with apparent molecular weight of 14–16 kD is observed which suggests that FRP is a dimer. FRP has been found to a dimer of two inhibin β chains. It may be a homodimer, either two $\beta_A$ chains or two $\beta_B$ chains, or it may be a heterodimer of a $\beta_A$ chain and a $\beta_B$ chain. Such inhibin β-chain dimers, and perhaps monomers which are unlinked to inhibin alpha chains, are functional antagonists of inhibin activity and may be administered to a mammalian animal to counteract endogenous inhibin and therefore act in a direction opposite to that of inhibin. Because of the very substantial homology between the inhibin β chains of different mammalian species, the FRP of one species should be biologically active in other mammalian species.

Purification of 28 kD porcine FRP to a purity of at least about 90% by weight of total protein in the fraction was achieved through a combination of protein separation procedures including salt precipitation, ultrafiltration, preparatory high-performance liquid chromatography (HPLC), gel filtration, cation exchange-fast protein liquid chromatography (FPLC), semi-preparatory HPLC, gel permeation-FPLC and analytical HPLC using a Vydac $C_8$ stationary phase and a TFA/$CH_3CN$ (trifluoroacetic acid/acetonitrile) gradient mobile phase.

BRIEF DESCRIPTION OF THE DRAWINGS

FIG. 3a, b, c and d show a series of elution profiles constituting the final purification of a FSH-releasing substance, termed activin, from porcine follicular fluid; more specifically, shown are the results of sequential chromatography of the material obtained from the Sephacryl S-200 purification, which was processed through (a) a Vydac $C_4$ semi-preparative column and eluted with acetonitrile in TEAP buffer, (b) a Vydac $C_4$ semi-preparative column and eluted with acetonitrile in TFA solvent system, (c) a Vydac phenyl semi-preparative column and eluted with acetonitrile in TEAP buffer, and (d) an Aquapore RP-300 $C_8$ analytical column and eluted with acetonitrile in TFA solvent system. The broken line indicates the gradient concentration of acetonitrile during the course of the run. The shaded area indicates FSH concentration per well determined by bioassay, as described herein, the activity being expressed as the nanograms (ng) of FSH released per well. The solid line represents the concentration of total protein eluted, as monitored at 210 or 280 nm using an ultraviolet detector.

DETAILED DESCRIPTION OF THE PREFERRED EMBODIMENTS

A protein, designated FRP, was discovered in mammalian follicular fluid which stimulates the secretion of FSH from cultured anterior pituitary cells but does not appear to stimulate the release of LH or any other known pituitary hormone. In this respect, the action of FRP is opposite to the action of inhibin, which inhibits basal secretion of FSH from cultured anterior pituitary cells but does not inhibit basal release of LH. The action of FRP is not blocked by known GnRH antagonists which interact with GnRH receptors, indicating that the biological activity of FRP is not through interaction with GnRH receptors. The protein can be isolated in a multi-step procedure to substantial homogeneity, i.e., greater than about 75% by weight of total endogenous protein, e.g. about 95%.

Figure 2:
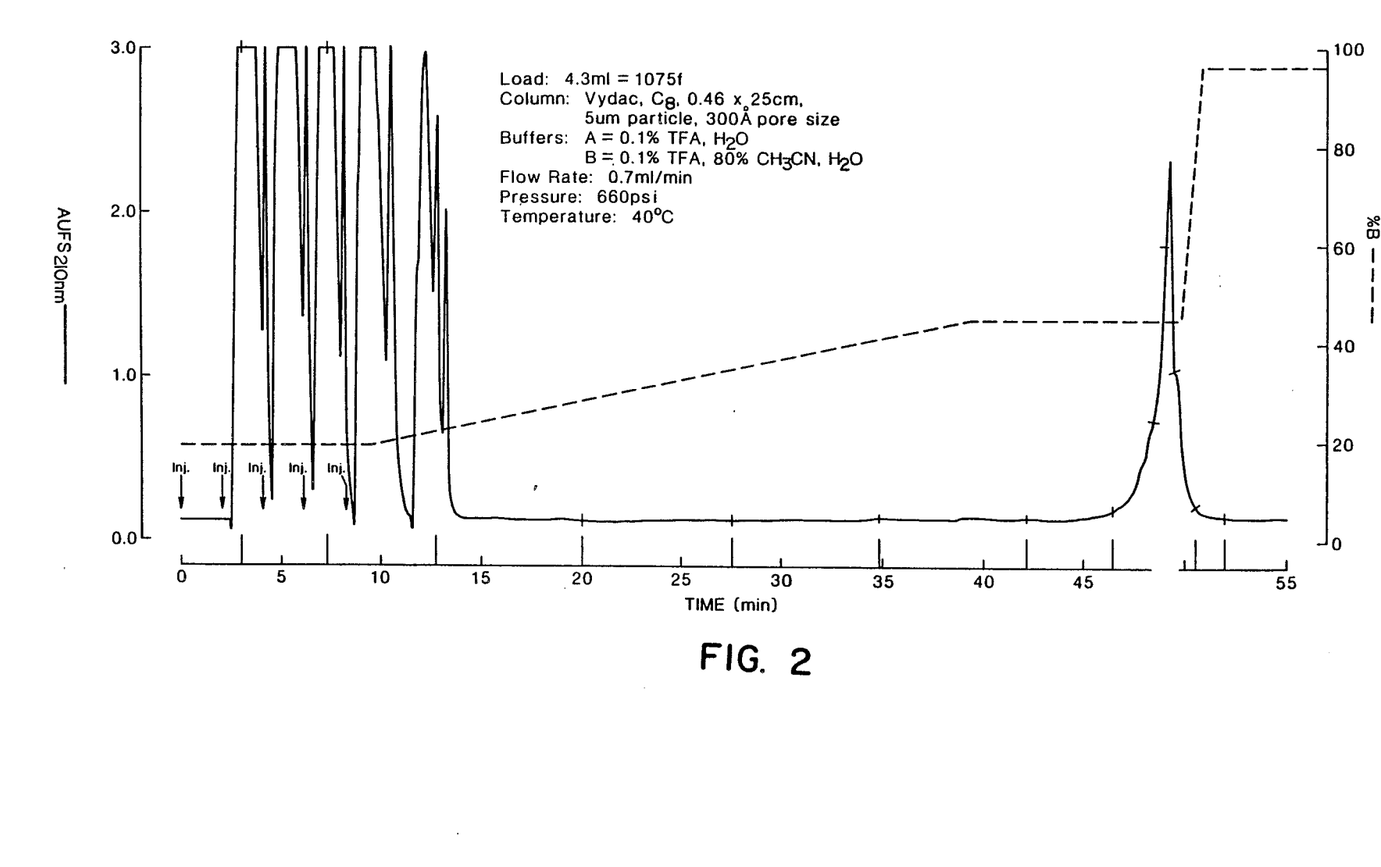
FIG. 2 is an elution profile of FRP during the final analytical reverse-phase, high-performance liquid chromatography (RP-HPLC) fractionation.

Physically, the major component has a molecular weight of about 28,000 daltons as determined by SDS-PAGE. Under reducing conditions, a predominant zone of approximately 14,000 daltons is seen, indicating that the protein is a dimer. At the end of a multi-step purification procedure, the protein is further characterized by means of analytical RP-HPLC using a stationary phase of Vydac $C_8$, 5 $\mu$m, in a 0.46×25 cm. column, and a gradient of buffer A, which is 0.1% aqueous trifluoroacetic acid (TFA), and buffer B, which is 0.1% TFA plus a mixture of water and acetonitrile (20:80). Unless otherwise noted, all ratios and percents are by volume. As shown in FIG. 2, the FRP material is loaded with an initial flow of 20% buffer B and a flow rate of 1.2 ml/min. After loading, the column is eluted at a flow rate of 0.7 ml/min. and a temperature of 40° C. so as to achieve a gradient which results in a 45% buffer B solution in 30 minutes. The protein elutes from the column, and at about 39 minutes after the starting the gradient, a single, sharp band is collected, which is tested for biological activity and potency and found to be FRP. It was then characterized by Edman degradation.

FRP was initially isolated from porcine follicular fluid (pFF), generally contemporaneously with isolation of inhibin, Rivier et al., *Biochem. Biophys. Res. Commun.* (1985) *supra*. Some chromatographic elution fractions of pFF were found to inhibit FSH secretion from anterior pituitary cells, i.e., they exhibited inhibin activity; whereas other fractions were found to stimulate the secretion of FSH by the cultured cells, and the active material in the FSH-stimulating fractions was designated FRP. Both FRP and inhibin fractions were further processed to isolate the active proteins, purified FRP being the subject of the present invention.

Briefly, the initial purification of FRP to substantial homogeneity utilized a salt precipitation step, an ultrafiltration step and a preparative HPLC step, which were part of the procedure by which porcine inhibin was purified from pFF. Dialyzed supernatant from a 50% ammonium sulfate precipitation of about 6 liters of pFF was ultrafiltered to remove protein having molecular weights below about 10 kD and then subjected to preparative HPLC using a Vydac $C_4$ stationary phase and a TEAP, pH 6.5 buffer, propanol gradient mobile phase as described earlier in Rivier et al., *Biochem. Biophys. Res. Commun.* (1985) *Supra*. FSH-releasing activity was observed in the early eluting, retarded fractions, and was thereby separated from the two major FSH-release-inhibiting (inhibin) zones, which were either not retarded or were eluted later.

Throughout the purification procedure, FRP activity in elution fractions was determined by a bioassay. The bioassay for FRP is based upon the ability of FRP to stimulate FSH secretion by cultured anterior pituitary cells as described in Vale et al. *Endocrinology*, 91, 562–572 (1972). Using this assay, half-maximal effective dosages ($EC_{50}$) are determined for FRP and FRP-containing fractions. The half-maximal effective dose is the concentration of protein that increases the basal secretion of FSH to one-half the plateau level of increased FSH secretion, i.e., where additional FRP does not further stimulate FSH secretion. The $EC_{50}$'s herein are based upon a plating of $5 \times 10^5$ pituitary cells incubated for 72 hours at 37° C. in 60×15 mm Falcon culture dishes containing 3 ml of Dulbecco modified Eagle's medium (DMEM) plus 100 $\mu$l of protein-containing solution.

The zones obtained from the preparative RP-HPLC which exhibited FSH-releasing activity in bioassay were pooled, lyophilized and redissolved in a strongly dissociating buffer which contained 6 M guanidine HCl. The solution was then gel filtrated by application to a Sepharose CL-6B column and FSH-releasing activity was eluted with the same buffer with over a $K_{AV}$ range of from 0.54 to 0.71. It was noted at this point that FRP behaved on gel filtration similarly to the 32K form of inhibin, which had fortunately been separated earlier by the preparative HPLC.

Figure 1:
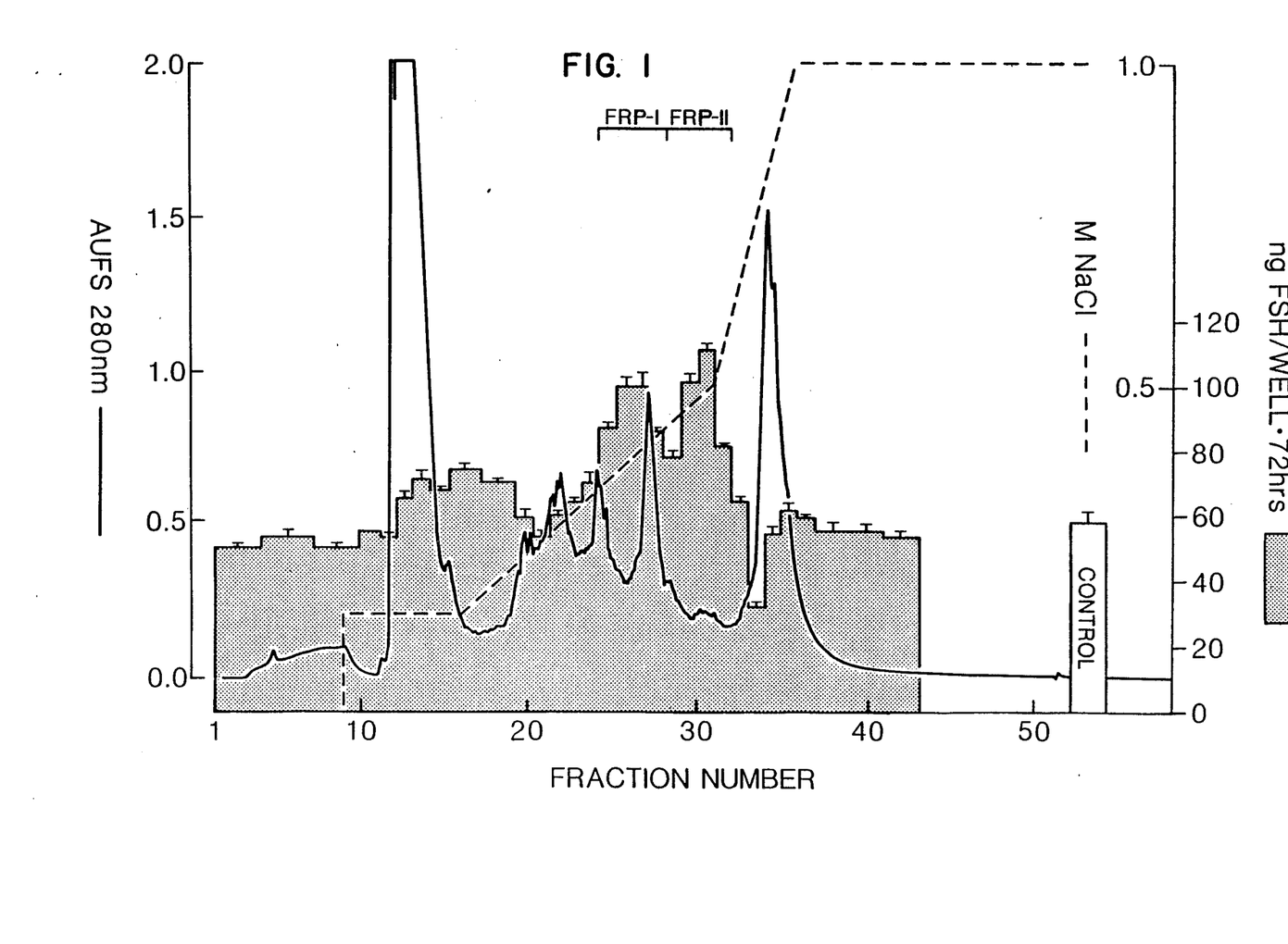
FIG. 1 is an elution profile of FRP on cation exchange chromatography. The broken line indicates the NaCl gradient concentration from 0 to 1.0M during the course of the run. The shaded area indicates FSH activity per well determined by bioassay, as described herein, the activity being expressed as the ng of FSH released per well at 72 hours. The solid line represents the concentration of total protein eluted as monitored at 280 nm using an ultraviolet detector.

The FSH-releasing fractions were pooled and dialyzed and then subjected to cation exchange chromatography on FPLC using a Mono-S stationary phase equilibrated in a solution of 4 M urea, 50 mM sodium acetate and eluted by a salt gradient of from 0 to 1M NaCl in the solution. Two regions of FSH-releasing activity were detected, FRP-I and FRP-II (FIG. 1).

The latter eluting FRP-II fraction had higher specific activity and was further purified by semi-preparative RP-HPLC using a Vydac $C_8$ column and a NaCl gradient in $TFA/CH_3CN$ solution. Active fractions from the semi-prep RP-HPLC were further purified by gel permeation on an FPLC Superose 12B column eluted with 6M guanidine HCl. Finally, FRP was isolated by two steps of analytical RP-HPLC using a Vydac $C_8$ column eluted with a $CH_3CN$ gradient in $TFA/CH_3CN$ solution. The FRP eluting from the final analytical HPLC produced a single peak of activity as seen in FIG. 2. On SDS-PAGE under reducing conditions, the protein in the pooled peak fractions ran as a single band, corresponding to a molecular weight of approximately 14 kD.

Highly purified FRP stimulates FSH secretion by cultured anterior pituitary cells in a dose-related fashion, exhibiting a half-maximal effective dose ($EC_{50}$) of ca. 25 pM, assuming a molecular weight of 28 kD. FRP does not stimulate the secretion of pituitary hormones LH, prolactin (Prl), growth hormone (GH) or adrenocorticotrophin (ACTH) and, in fact, slightly suppresses basal release of GH and ACTH.

The isolation of 28 kD porcine FRP to substantial homogeneity is now described in greater detail by way of specific example.

EXAMPLE

Bioassay of FSH-releasing activity, indicating the presence of the FRP in elution fractions throughout the purification, was performed as follows. Rat anterior pituitary glands were enzymatically dissociated and the cells plated in a monolayer of $3.3 \times 10^5$ cells per well in B-PJ medium in 2% FBS. After washing the cells 3 times with the same medium, aliquots of eluants were added and allowed to remain on the cells for 48-72 hours, at which time fluids were removed from the cells and assayed for FSH using a radioimmunoassay kit provided by the National Hormone and Pituitary Program of NIADDK. For testing elution fractions of RP-HPLC columns, aliquots for assays (0.1-1.0% of total fraction volume, but never less than 5 $\mu$l) were measured with micropipettes and plastic tips and were transferred into polypropylene tubes containing bovine serum albumin (10 $\mu$l of 10 mg/ml) and dried in a Savant rotary evaporator. For testing elution fractions of gel permeation and ion exchange columns where desalting was necessary prior to assay, small aliquots were removed and transferred into glass tubes containing 0.5 ml of 10 mM Hepes plus 0.1% BSA, pH 7.5. Squares of dialysis tubing with MW cutoff of ca. 1000 were secured over the tops with rubber bands. The tubes were inverted and dialyzed against 10 mM Hepes, pH 7.5. The retentates were then dried using a Savant rotary evaporator. All fractions were resuspended in the cell culture assay medium.

The starting material for the procedure, porcine follicular fluid (6050 mls), was supplied frozen by the Contraceptive Development Branch of NICHD. The material was thawed and centrifuged at $700 \times g$ for 5 minutes in order to separate cell debris.

The crude supernatant was initially purified by ammonium sulfate salt precipitation. To the crude supernatant was added dropwise over 2-3 hours an equal volume of Schwartz/Mann ultrapure 100% saturated ammonium sulfate adjusted to pH 7.8 with ammonium hydroxide. The mixture was centrifuged at $8200 \times g$ for 30 minutes, and the supernatant and precipitate were separated. The supernatant was retained.

The supernatant was ultrafiltered and concentrated using a Millipore Pellicon Cassette system with 5 sq. ft. of filter of 10,000 MW cutoff at a rate of 300 ml/min. using a peristaltic pump with back pressure applied until filtration rate was 20 ml/min. The total retentate was washed several times with 10 mM Hepes and 0.05% dimethyl sulfide, pH 7. The final retentate (6,050 ml-eq in 2,240 ml.) was collected. The protein concentration of the retentate was 10 mg/ml-eq. The term "ml-eq" is used to indicate a given amount of biologically active protein material which is derived from 1 ml of pFF.

The concentrated retentate was next purified by preparative RP-HPLC. In each run, 500 ml-eq of protein or less were processed on a Waters Prep 500Å using Vydac end-capped $C_4$ silicas, 15-20 $\mu$M particle size in a $5 \times 30$ cm cartridge. The column temperature was thermostated at 60° C. Buffer A was 0.1% $H_3PO_4$, 0.28% TEA, pH 6.5; buffer B was 60% n-propanol in buffer A. Columns were loaded at 20% buffer B; the gradient used was 20% buffer B to 65% buffer B in 45 min. Flow rate was 75 mls/min. FSH-releasing activity eluted between retention volumes (RV) 825 and 1350 mls from the start of the gradient. Active zones from preparative RP-HPLC were pooled and lyophilized. The protein concentration was 700 $\mu$g/ml-eq; and on bioassay, the $EC_{50}$ was 2.8 $\mu$g/ml.

The pooled fractions from the preparative RP-HPLC were further purified by gel permeation FPLC on a $10 \times 120$ cm (8600 ml.) Sepharose CL-6B column. The pooled fraction was brought up to 6M in guanidine HCl, 0.1M ammonium acetate, 0.05% dimethyl sulfide, pH 4.75. The eluant was 0.22 $\mu$m filtered and degassed before use. The flow rate was 180 mls/hr. FSH-releasing activity eluted between $K_{AV}$ 0.54 and 0.71. The pooled retentate of active fractions had a protein concentration of 130 $\mu$g/ml-eq and an $EC_{50}$ of 730 ng/ml.

The active fractions from gel permeation chromatography were pooled and dialyzed against Milli Q $H_2O$ plus 0.01% dimethyl sulfide using tubing with a MW cutoff of about 1000, and the fractions were lyophilized. The pooled retentate from the gel permeation was then further purified by cation exchange FPLC. Cation exchange was conducted using a Pharmacia FPLC system equipped with a Mono S HR 16/10 column, $V_t = 20$ ml. The mobile phase was a gradient of buffer A: 50 mM sodium formate, 4M urea, 1 mM 3-[(Cholamidopropyl)-dimethylammonio]-1-propanesulfonate (CHAPS) in Milli Q $H_2O$, pH 4.3, and buffer B: 1M NaCl in buffer A. Buffers were 0.22 $\mu$m filtered and degassed before use. The lyophilized retentate was dissolved in buffer A and processed in three equal batches. Flow rate was 8 mls. per minute, and the gradient was as shown in FIG. 1. In particular, for 9 min. the eluant was 100% buffer A; at 9 min. the buffer was abruptly changed to 15% buffer B and held thereat over a period from 32 to 36 min., the gradient was linearly increased from 15% buffer B to 50% buffer B; and in a period from 36 to 50 min., the buffer was linearly changed from 50% buffer B to 100% buffer B and the column was eluted at 100% buffer B thereafter.

Two biologically active zones of FRP, relative to baseline FSH-secretion, resulted from the cation exchange FPLC chromatography. The zone eluting from ca. 0.34-0.43M NaCl is designated FRP-I. The later zone which eluted from ca. 0.43-0.60M NaCl is designated FRP-II and was the more active fraction. Pooled FRP-II fractions had a protein concentration of 8 $\mu$g/ml-eq and an $EC_{50}$ of 96 ng/ml.

Each of the pooled FRP-I and FRP-II eluates was further purified and desalted by semi-preparative RP-HPLC, using a Beckman HPLC and $1 \times 30$ cm Vydac columns packed with end-capped $C_8$ silicas, 5 $\mu$m particle size. The eluant was a gradient of buffer A: 0.1% TFA and buffer B: 80% $CH_3CN$ in 0.1% TFA. For FRP-I, columns were thermostated at 40° C. and run at 2.5 ml/min. isocratically at 25% buffer B for 17 min., followed by a linear gradient to 55% buffer B in 30 min. Activity eluted between retention volumes 60 and 65 from the start of the gradient. The protein concentration of the FRP-II was 700 ng/ml-eq and the $EC_{50}$ on bioassay was 25 ng/ml.

Active zones from semi-preparative RP-HPLC of FRP-I and FRP-II were separately processed by gel permeation on the Pharmacia FPLC system using tandem Superose 12B columns, 10 $\mu$m, $10 \times 300$ mm each. Column eluant was 6M guanidine HCl, 0.1M ammonium acetate, 0.05% dimethyl sulfide, pH 4.75 in Milli Q $H_2O$. The eluant was 0.22 $\mu$m filtered and degassed before use. Flow rate was 4 ml/min. In each case, activity was eluted between $K_{AV}$ 0.26 and 0.31. Pooled FRP- II fractions had a protein concentration of 300 ng/ml-eq and an $EC_{50}$ of 5 ng/ml.

The pooled active zones of FRP-II recovered from the FPLC gel permeation were processed by analytical RP-HPLC using a Vydac $C_8$, 5 μm, 0.46×25 cm column using the Beckman system, thermostated at 40° C. Buffer A was 0.1% TFA, buffer B was 0.1% TFA and a mixture of water and acetonitrile (20:80). Approximately 1,000 ml-eq were loaded at a time, starting initially at 20% buffer B and a loading flow rate of 1.2 ml/min. Injection volume was 4.3 mls in five equal injections. The gradient was run to 45% buffer B in 60 minutes after loading with a flow rate of 0.7 ml/min. Active fractions were pooled, and this step was repeated with the gradient being reduced to 30 minutes. The pooled fractions from this second step eluted as a single peak about 39 minutes after the gradient was begun, as seen in FIG. 2. Protein concentration was 20 ng/ml-eq, and $EC_{50}$ was 1 ng/ml. Thus ca. 100 μg of substantially homogeneous FRP protein is recovered from 390 gm. of total protein in the starting 6050 ml of pFF.

An aliquot of the highly purified FRP was subjected to Edman degradation. The first 32 residues of N-terminal sequence of the intact FRP were found to be identical to the N-terminal sequence of the porcine inhibin $\beta_A$-chain, i.e., Inhibin $\beta_A$ (1–32) or residues 309–340 (based on numbering in the pre pro form, Mason et al. supra.). Another aliquot of the FRP was reduced, S-carboxymethylated and subjected to HPLC. The major peak from HPLC was digested by clostripain, and the fragments, following HPLC purification, were subjected to Edman degradation. The sequences of certain fragments were found to be identical to residues 75–85, 88–102 and 103–116 of porcine inhibin $\beta_A$. This purified FRP exhibits a major band at ca. 28 kD on SDS-PAGE, which following reduction converts to a major zone of ca. 14–16 kD. These results are consistent with the conclusion that FRP-II is a homodimer consisting of two inhibin $\beta_A$ chains linked by disulfide bonds. A second, very similar peptide, termed activin, was isolated from additional porcine follicular fluid(pFF) also contemporaneously with the isolation of inhibin which was described in Ling et al., P.N.A.S. (1985) supra. Some chromatographic elution fractions of pFF were found to inhibit FSH secretion from anterior pituitary cells, i.e., they exhibited inhibin activity. However, other fractions were found to stimulate the secretion of FSH by the cultured cells, and the active material in these FSH-stimulating fractions is referred to hereinafter as activin. The activin fractions were further processed to isolate the active proteins and thereby provide purified activin.

In purification procedure used, porcine activin was isolated from crude extract material obtained from a porcine animal body, specifically porcine follicular fluid (pFF), although other appropriate bodily extracts might be used. Successive purification procedures included heparin-Sepharose affinity chromatography, gel filtration and at least one and preferably several RP-HPLC separations using different conditions, i.e., stationary phase and/or mobile phase. The same procedure is useful in obtaining a desired mammalian activin protein from a crude extract resulting from recombinant DNA processes.

In the procedure by which activin was isolated to substantial purity, pFF was first purified by heparin-Sepharose affinity chromatography, next by gel filtration on Sephacryl S-200 gel and then with four successive RP-HPLCs using different mobile phase gradients and/or derivatized silica supports. Stationary phases having relatively low hydrophobicity are used, with $C_3$–$C_8$ columns being preferred, and $C_3$–$C_5$ and phenyl columns being particularly preferred. Solute specificity of the mobile phase is preferably adjusted by varying the concentration of an organic component, particularly acetonitrile. Although a single RP-HPLC fractionation significantly increases the purity relative to the gel-filtrated material, two or more, and preferably four, RP-HPLC purifications are performed subsequent to successive treatment by heparin-Sepharose chromatography and gel filtration.

The starting material for the procedure was frozen pFF that was procured from J. R. Scientific, Woodland, Calif. Approximately 2 liters of such frozen pFF were processed in 500 ml batches to isolate the activin product. The first step of the purification was heparin-Sepharose affinity chromatography, in which the protein is adsorbed to the Sepharose-bound heparin moieties under application conditions, and the adsorbed activin and inhibin material is recovered by 1 M NaCl elution. This step greatly expedites the purification of crude extracts because it allows a relatively large volume of a crude extract, such as pFF, to be processed fairly rapidly while recovering an amount of protein exhibiting total activin and inhibin activity equal to at least 90% of that of the crude extract.

Throughout the purification procedure, the activin and inhibin bioactivities were monitored by an in vitro bioassay using rat anterior pituitary monolayer culture, Ling, N. et al. P.N.A.S. (USA), 82, 7217–7227 (1985). In brief, 21-day-old female rat anterior pituitaries are collected, enzymatically dispersed and plated in 10% fetal bovine serum in HDMEM (GIBCO Laboratories, Santa Clara, Calig.) into 24-well tissue culture plates (Falcon Plastic, Oxnard, Calif.) on day 1. On day 2, the medium is changed to 1% fetal bovine serum in HDMEM, and the sample is added. Incubation is continued for another 48 hours. The medium is then harvested, and the LH and FSH contents are determined by radio-immunoassay (RIA) using materials provided by The Pituitary Hormone Program of NIADDKD. In this assay, the inhibin proteins inhibit the basal release of FSH only but not that of LH; as compared to control cells that receive the incubation medium only, the activin proteins release FSH above basal level.

For the detection of activin and inhibin activity in the various column fractions, aliquots ranging from 0.01% to 0.1% by volume were removed, and after adding 100 μg human serum albumin in 100 μl water, the solvents were evaporated in a Speed-Vac concentrator (Savant, Hicksville, N.Y.). The residue was redissolved in 3 ml 1% fetal bovine serum in HDMEM, filtered through a Millex-GS 0.22 μm filter (Millipore Corp., Bedford, Mass.) and assayed in duplicate.

To perform the heparin-Sepharose affinity chromatography, a 500 ml bottle of frozen pFF was defrosted, and the cell debris were spun down in a Beckman J2-21 centrifuge (Beckman Instruments, Inc., Palo Alto, Calif.) using a JA-20 rotor at 10,000 rpm for 30 minutes. The supernatant (480 ml) was diluted to about 10 times its volume by the addition of 3,500 ml of 0.01 M Tris-HCl containing 0.1 M NaCl, pH 7, in a 4 liter Erlenmeyer flask and pumped simultaneously via eight silastic tubes (0.76 mm ID) into eight heparin-Sepharose (Pharmacia Fine Chemicals, Piscataway, N.J.) columns (3.5×9 cm) by two Rabbit 4-channel peristaltic pumps (Rainin Instrument Co., Inc., Emeryville, Calif.) at 40 ml/hr per column. After all the fluid had been pumped through the heparin-Sepharose, the eight columns were washed simultaneously with 3.5 liters of 0.01 M Tris-HCl, pH 7, containing 0.1 M NaCl, in the same manner. The adsorbed proteins with activin and inhibin activities were removed by washing the eight columns simultaneously with 1.3 liters of 0.01 M Tris-HCl containing 1 M NaCl, pH 7, as above, and the wash was collected into fractions of 16 ml. The activin and inhibin activities were monitored by the in vitro bioassay described above. The columns were regenerated by further washing with 1.6 liters 2 M NaCl in 0.01 M Tris-HCl, pH 7, and re-equilibrated with 3.5 liters 0.01 M Tris-HCl containing 0.1 M NaCl.

The fractions having activin and inhibin activities extracted by the eight heparin-Sepharose columns were pooled (400 ml) and dialyzed overnight to remove NaCl in a 28.6 mm cylinder diameter Spectrapor No. 3 membrane tubing with $M_r$ cutoff at 3,500 (Spectrum Medical Industries, Inc., Los Angeles, CA.) against 16 liters of 30% acetic acid. The retained fluid was centrifuged, as above, to remove a white precipitate, and the supernatant was divided into eight equal portions for applying to eight 5×100 cm Sephacryl S-200 superfine gel filtration columns (Pharmacia Fine Chemicals, Piscataway, N.J.) to separate proteins generally according to their molecular weights. Each column was eluted with 30% acetic acid at 20 ml for 22 min., and the column fractions were monitored by UV absorption at 210 and 280 nm and by bioassay. The fractions containing the FSH-releasing activity eluted from Sephacryl S-200 columns after the inhibin material.

Figure 3A:
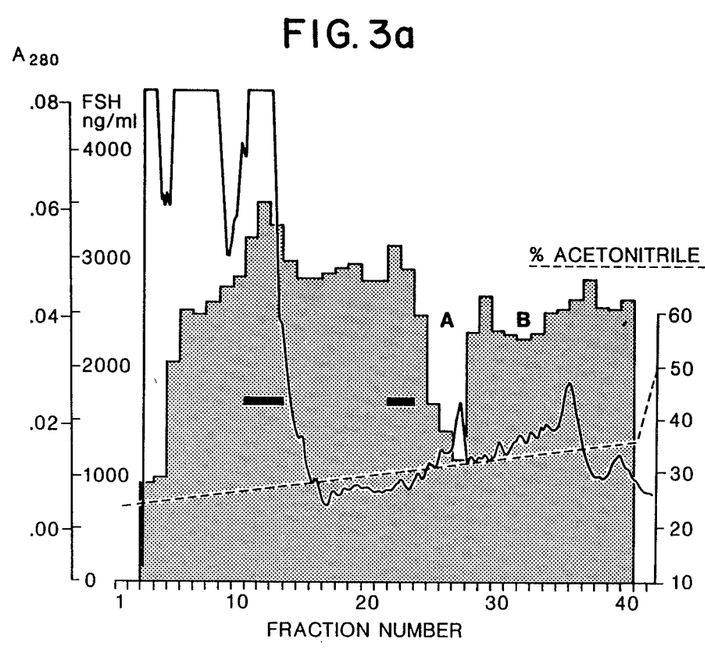

The proteins from the eight S-200 columns were pooled and lyophilized. The lyophilized material (about 50 mg) was dissolved in 40 ml 0.2N acetic acid and filtered through a Millex-HA 0.45 μm filter (Millipore Corp., Bedford, MA.). The filtrate was applied directly onto a 1×25 cm Vydac 5-μm particle-size C4 column (The Separations Group, Hesperia, CA.) and developed with a gradient of TEAP buffer as shown in FIG. 3a. In the TEAP system, buffer A consists of 0.25 N. triethylammonium phosphate, (TEAP) pH 3, and buffer B is 80% acetonitrile in buffer A (Vol/Vol). After all the filtrate had been loaded, the column was washed with the aqueous buffer A until the UV absorption reached baseline. The fractions exhibiting inhibin and FSH-releasing activities were separated using a Beckman 322 gradient liquid chromatography system (Beckman Instruments, Inc., Berkeley, CA.) equipped with a Spectroflow 757 UV detector (Kratos Analytical Instruments, Ramsey, N.J.), a Soltec 220 recorder (Soltec Corp., Sun Valley, CA.) and a Redirac 2112 fraction collector (LKB Instruments, Inc., Gathersburg, MD.). Two zones of substantial inhibin activity were detected, designated Inhibin A and Inhibin B, as well as two zones of FSH-releasing activity denoted by the two solid bars in FIG. 3a.

Figure 3B:
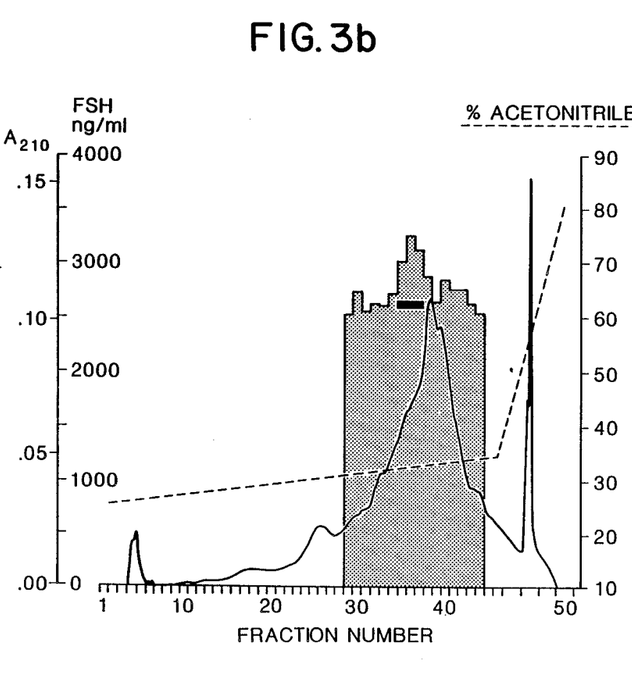
Figure 3C:
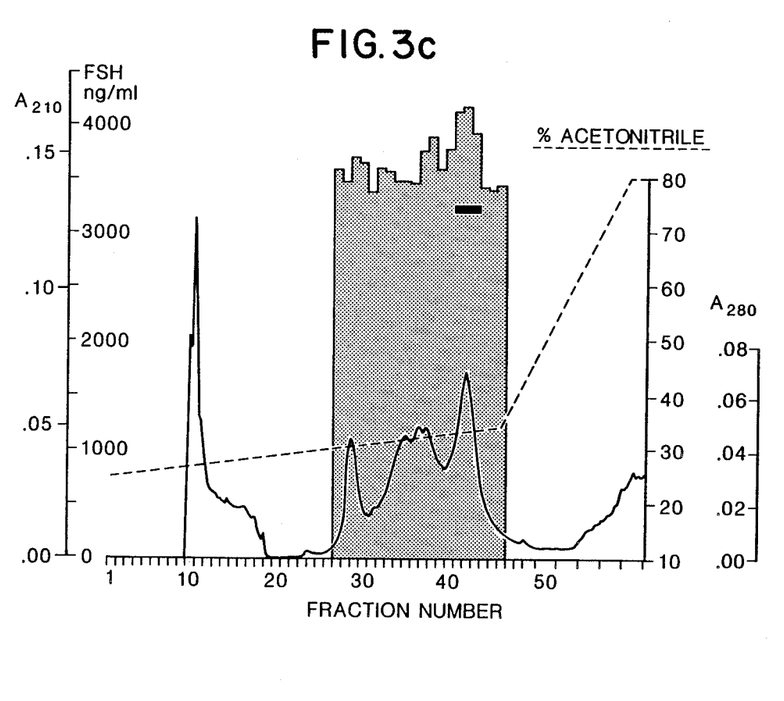
Figure 3D:
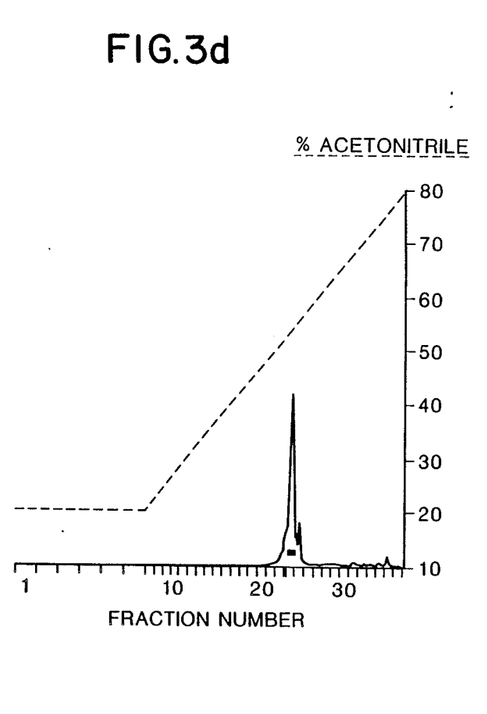

The FSH-releasing fractions denoted by the right hand solid bar in FIG. 3a, which eluted at 30% acetonitrile, were pooled and further purified by two more RP-HPLC steps after mixing with an equal volume of 0.2 N acetic acid. The first step uses a 1×25 cm Vydac 5-μm-particle-size C4 column, a trifluoroacetic acid (TFA) buffer system (FIGS. 3b) and a flow rate of 6 ml. per 2 minutes. In the TFA system, buffer A contains 1 ml trifluoracetic acid in 999 ml water, and buffer B is 1 ml trifluoroacetic acid in 199 ml water and 800 ml acetonitrile. The active material, denoted by the solid bar in FIG. 3b, is pooled, similarly diluted to twice its volume and chromatographed on a 1×25 cm Vydac 5-μm-particle-size Phenyl column using the TEAP buffer system, as shown in FIG. 3c, and using a flow rate of 2 ml. per 2 minutes. Finally, the protein accumulated from four chromatographic batches, as shown in FIG. 3c, was similarly diluted to twice its volume and subjected to RP-HPLC using a 0.46×25 cm Aquapore RP-300, 10 μm-particle-size column (Brownlee Labs., Santa Clara, CA.) and the TFA buffer system as shown in FIG. 3d, at a flow rate of about 0.5 ml. per minute. Altogether, a total of approximately 32 μg of activin was purified from the 2 liters of pFF.

The activin from the final RP-HPLC purification was analyzed under reducing and non-reducing conditions in 1-mm-thick 15% acrylamide gel according to the method of Laemmli, V., Nature 227 680–685 (1970). The protein was revealed by a Coomassie blue staining reagent (BIO-RAD, Richmond CA.). The following molecular weight standards were used to calibrate the gel: bovine serum albumin ($M_r$=67,000), ovalbumin ($M_r$=43,000), alpha-chymotrypsinogen ($M_r$=25,700) and lysozyme ($M_r$=14,500). For non-reducing conditions, one μg of activin protein in 20 μl water was incubated with 20 μl sample buffer (0.125 M Tris-HCl, pH 6.8, containing 20% glycerol (V/V), 4% sodium dodecylsulfate and 0.04% bromphenol blue) for 1 hour at 37° C. prior to loading onto the gel. The electrophoresis was performed at a constant 200 volts for 6 hours at room temperature. For reducing conditions, 1.5 μg of protein was incubated, first with 20 μl of 0.02 M dithiothreitol for 15 min at 37° C., and then 20 μl of sample buffer was added and the incubation continued for one more hour before the sample was applied to the gel. Electrophoresis was carried out as above, except that 0.005 M dithiothreitol was included in the electrophoretic buffer. On SDS-PAGE under non-reducing condition, activin protein showed a single band migrating at $M_r$ about 24,000. Under reducing conditions, activin separates into two bands, one migrating at $M_r$ about 14,700 and the other $M_r$ about 13,800. Electrophoresis of the β chains of Inhibin A and Inhibin B under the same conditions showed two very similar bands.

Figure 4A:
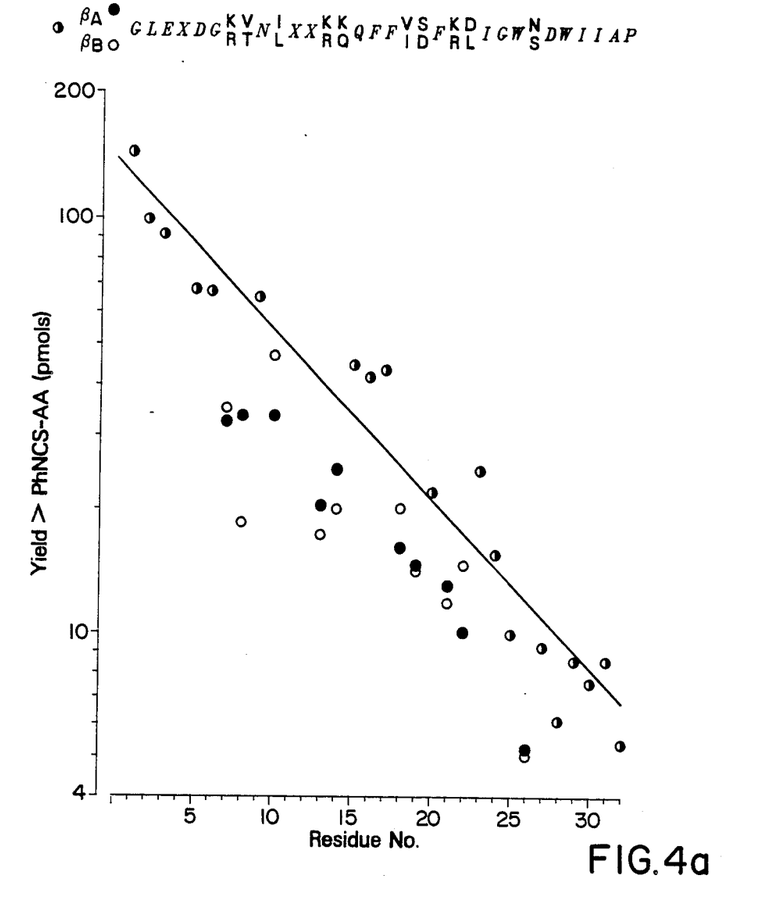
FIG. 4a shows the results the N-terminal sequencing of about 200 picomoles of activin using an Applied Biosystems Inc. 470A protein sequencer, with the released PTH-amino acids being analyzed by the 120A PTH-analyzer. A residue common to each chain is denoted by a half-filled circle, whereas unique residues present only in the $\beta_A$ chain are designated by a filled-in circle and residues present in only the $\beta_B$ chain are designated by an empty circle. The conclusion appears at the top of FIG. 4a, where an "X" appears where the identity of residue could not be determined, which is consistent with Cys being present in that position, as can be seen from FIG. 4b which shows the sequences of porcine inhibin $\beta_A$ and $\beta_B$ deduced from molecular cloning.
Figure 4B:
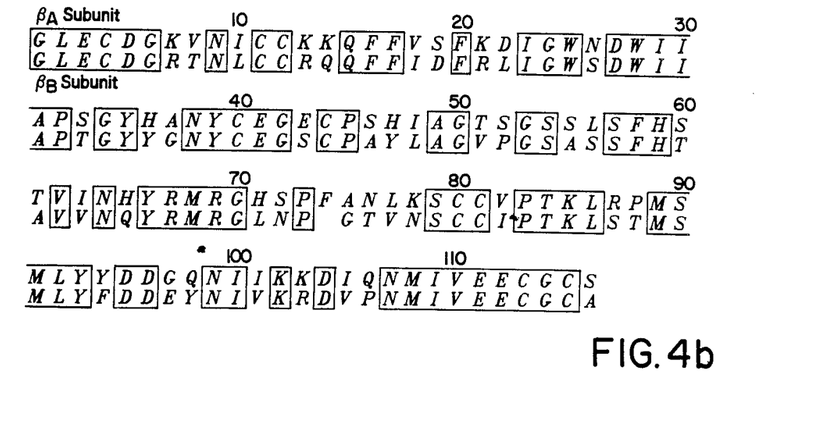

The results of microsequencing, as described in Esch, F. Anal. Biochem. 136, 39–47, 1984, of intact activin protein beginning at the NH$_2$-terminus are illustrated in FIG. 4a. The data obtained is consistent with the theoretical results of sequencing approximately equal concentrations of the $\beta_A$ and the $\beta_B$ chains of inhibin. Cysteine is destroyed in the sequencing process, thus the blank which appears is consistent with the presence of Cys in that position. Based upon the results from sequencing analyses of the intact activin protein and the knowledge of the β-chains of porcine inhibin, it could be determined that the NH$_2$-terminal residues of one chain of activin are: Gly-Leu-Glu-Cys-Asp-Gly-Lys-Val  Asn-Ile-Cys-Cys-Lys-Lys-Gln-Phe-Phe-Val-Ser-Phe-Lys-Asp-Ile-Gyl-Trp  Asn-Asp-Trp-Ile-Ile-Ala-Pro, and the NH$_2$-terminal residues of the other chain of activin are: Gly-Leu-Glu-Cys-Asp-Gly-Arg-Thr-Asn-Leu-Cys-Cys-Arg  Gln-Gln-Phe-Phe-Ile-Asp-Phe-Arg-Leu-Ile-Gly-Trp-Ser-Asp-Trp-Ile -Ala-Pro.

Based both upom the migration behavior of the reduced protein and the microsequencing, it is believed that activin is a heterodimer of the β subunits or chains of Inhibins A and B.

Highly purified activin stimulates FSH secretion by cultured anterior pituitary cells in a dose-related fashion, exhibiting a half-maximal effective dose ($EC_{50}$) of ca. $3.7\pm0.5$ ng protein/ml of medium (or ca. $1.5\times10^{-10}$M, assuming a molecular weight of 27,500 kD) and a maximal release at 16 ng/ml or higher. Activin does not stimulate the secretion of LH. Inhibin and activin are functionally competitive, but inhibin is not a competitive antagonist to activin because it does not appear to act upon the same receptors.

FRP and activin are distinguished in activity from GnRH in several ways. Although FRP and activin are potent releasers of FSH, they have no effect on the secretion of LH, whereas GnRH releases both gonadotropins. GnRH acts immediately to stimulate gonadotropin secretion, whereas the onset of action by FRP or activin is delayed by from 4 to 24 hours and neither is maximally effective until more than 24 hours after treatment. However, pituitary cells treated with maximal concentrations of FRP or activin for 72 hours secrete as much FSH during that period as those exposed to plateau levels of GnRH.

GnRH receptor antagonists, which in vitro completely prevent the release of FSH and LH that is attributable to GnRH, have no effect on the secretion of FSH mediated by FRP or activin. These results strongly indicate that they act independently of the GnRH receptor.

Whereas prolonged exposure of pituitary cells to GnRH results in considerable depletion of cellular FSH stores, FRP and activin, which mediate the release of similar amounts of FSH into the medium, actually increase the amounts of stored FSH within the cells. Both FRP and activin, therefore, appear to have greater effect on the biosynthesis of FSH than does GnRH.

Purified porcine inhibin lowers baseline production of FSH and therefore obscures the effects of modest concentrations of either FRP or activin. Inhibin and either FRP or activin are functionally competitive, but each acts independently, i.e., in absence of the addition of the other.

Porcine FRP is a homodimer of two inhibin $\beta_A$ chains of 116 residues each of the following formula, interconnected by disulfide bonding:

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH.

Synthetic dimers of two subunits of inhibin $\beta_B$, each of which has the formula:

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—Ser—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—

-continued
Lys—Arg—Asp—Val—Pro—Asn—Met—Ile—Val—Glu—
Glu—Cys—Gly—Cys—Ala—OH, also have FSH-releasing biological activity.

Porcine activin is a heterodimer where one chain has the formula of inhibin $\beta_A$, i.e.:

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH, and the other chain has the formula: H—Gly—Leu—Glu—Cys—Asp—Gly—Arg—Thr—
Asn—Leu—Cys—Cys—Arg—Gln—Gln—Phe—Phe—Ile—
Asp—Phe—Arg—Leu—Ile—Gly—Trp—Ser—Asp—Trp—
Ile—Ile—Ala—Pro—Thr—Gly—Tyr—Tyr—Gly—Asn—
Tyr—Cys—Glu—Gly—Ser—Cys—Pro—Ala—Tyr—Leu—
Ala—Gly—Val—Pro—Gly—Ser—Ala—Ser—Ser—Phe—
His—Thr—Ala—Val—Val—Asn—Gln—Tyr—Arg—Met—
Arg—Gly—Leu—Asn—Pro—Gly—Thr—Val—Asn—Ser—
Cys—Cys—Ile—Pro—Thr—Lys—Leu—Ser—Thr—Met—
Ser—Met—Leu—Tyr—Phe—Asp—Asp—Glu—Tyr—Asn—
Ile—Val—OH.

Although the description hereinbefore has been primarily in terms of porcine FRP and activin, there is very strong homology between various vertebrate inhibin $\beta$ chains, particularly mammalian inhibin $\beta$ chains, e.g., porcine, human, ovine, bovine, etc. The 116-residue $\beta_A$ chains of porcine inhibin, human inhibin, bovine inhibin and rat inhibin have precisely the same formula, and it appears that ovine inhibin is likewise the same. Moreover, the formulae of porcine inhibin $\beta_B$ and its human $\beta_B$ counterpart have only one difference out of 115 residues, i.e., Ser in the 26-position instead of Asn for the human version. Accordingly, such vertebrate $\beta$-chain dimers surely have biological cross-reactivity between vertebrate species in stimulating FSH secretion.

These FSH-releasing proteins are useful for regulating gonadotropin secretion and thus fertility and or sex hormone production of both male and female mammalians, including humans. Although the proteins isolated were of porcine origin, they are believed to be biologically active throughout the genus of mammals, as have been the other neuroregulatory hormones previously isolated, characterized and thereafter synthetically reproduced. The dimeric inhibin $\beta$-chains of all vertebrate species, including humans, should exhibit such FSH-releasing activity. As set forth above, the $\beta$-chains for porcine and human Inhibin A have precisely the same 116-residue sequence, and there is only one amino-acid residue difference between the $\beta$-chains of porcine and human Inhibin B, which appears in the 26-position. Moreover, it is believed that the $\beta_B$ chain (in either the heterodimer or the homodimer) can be shortened by up to about 15 residues at its C-terminus without losing its biological activity and that the $\beta_A$ chain can be likewise shortened.

Thus, the invention provides a synthetic protein produced by recombinant DNA techniques or the like which is a heterodimer or a homodimer, having two chains interconnected by disulfide bonding, each chain having either the formula (a):

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH; or the formula (b): H—Gly—
Leu—Glu—Cys—Asp—Gly—Arg—Thr—Asn—Leu—Cys—
Cys—Arg—Gln—Gln—Phe—Phe—Ile—Asp—Phe—Arg—
Leu—Ile—Gly—Trp—R$_{26}$—Asp—Trp—Ile—Ile—Ala—Pro—
Thr—Gly—Tyr—Tyr—Gly—Asn—Tyr—Cys—Glu—Gly—
Ser—Cys—Pro—Ala—Tyr—Leu—Ala—Gly—Val—Pro—
Gly—Ser—Ala—Ser—Ser—Phe—His—Thr—Ala—Val—
Val—Asn—Gln—Tyr—Arg—Met—Arg—Gly—Leu—Asn—
Pro—Gly—Thr—Val—Asn—Ser—Cys—Cys—Ile—Pro—
Thr—Lys—Leu—Ser—Thr—Met—Ser—Met—Leu—Tyr—
Phe—Asp—Asp—Glu—Tyr—Asn—Ile—Val—Lys—Arg—
Asp—Val—Pro—Asn—Met—Ile—Val—Glu—Glu—Csy—
Gly—Cys—Ala—OH, wherein $R_{26}$ is Ser or Asn. Instead of the complete chains, a biologically active fragment of either chain or both may be used. For example, a continuous sequence of up to about 15 residues can be deleted from formula (b), beginning with the C-terminal residue, i.e. inhibin $\beta_B$ (1-100). It is believed that a similar deletion can be made to the $\beta_A$ chain without destroying biological activity.

Activin can be prepared by recombinant DNA methods, such as those generally described in co-pending U.S. patent application Ser. No. 784,436, filed Oct. 3, 1985, now U.S. Pat. No. 4,740,587, issued Apr. 26, 1988, and published European patent application 222,941A1, May 20, 1987, the U.S. equivalent of which issued as U.S. Pat. No. 4,798,885, disclosures of both of which are incorporated herein by reference. The monomers, which are substantially the $\beta$-chains of inhibin, are not themselves active, as activity is exhibited only in the dimer state. The dimers can be completely synthesized by expression in a suitable vector system, for example, by inserting genes for the desired pair of chains. Suitable mammalian cell lines, e.g., Chinese hamster ovarian cells, can express and process such proteins to create the biologically active dimers. Alternatively, the dimers, either homodimers or heterodimers, can be synthesized from monomers previously expressed in suitable vectors. Such monomers, synthesized by expression in suitable vectors, may also be allowed to dimerize by auto-oxidation.

The 28 kD FRP or activin protein is useful for regulating gonadotropin secretion and thus fertility and or sex hormone production of both male and female mammalians, particularly humans. Although the proteins isolated were of porcine origin, they are believed to be also biologically active throughout the genus of mammals, as have been the other neuro-regulatory hormones previously isolated, characterized and thereafter synthetically reproduced. It is conceivable that this gonadal dimer has a wider distribution that might include the hypothalamus, and it is also possible that it plays important autocrine, paracrine and/or hormonal roles in the regulation of gonadal and perhaps other functions. The high potency of the dimer on pituitary cells to modulate hormone secretion supports the regulatory potential of this protein.

The substantially pure 28 kD protein or biologically active portions thereof, combined with a pharmaceutically acceptable carrier to form a pharmaceutical composition, may be administered to mammals, including humans, either intravenously, subcutaneously, percutaneously, intramuscularly or orally for control of fertility, gonadotropin secretion or sex hormone production. In particular, this FSH-releasing dimer holds promise for increasing male and female fertility both in man and other mammals.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as polylactide/glycolides, tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Such peptides should be administered under the guidance of a physician, and pharmaceutical compositions will usually contain an effective amount of the peptide in conjunction with a conventional, pharmaceutically-acceptable carrier. The dosage will vary depending upon the specific purpose for which the peptide is being administered, and daily dosage levels in the range of about 0.1 to about 2 milligrams per Kg. of body weight may be used when administered on a regular basis for fertility regulation. It appears that the peptide will also be useful in treating infertility caused by low FSH production. Radioimmunoassays specific for the peptide would be helpful in the diagnosis of fertility disorders in males and females.

Although the method of purification of these peptides has been described primarily in terms of isolation from pFF, they can be similarly purified from other crude extracts, including human follicular fluid. It is anticipated that the $\beta$-chain monomers will be synthesized by recombinant DNA techniques in suitable cloning vectors. In certain suitable vector systems, dimers are completely synthesized. In other cases, the monomers maybe expressed by the vector systems and then dimerized in vitro. Alternatively, it is conceivable that fragments of the FSH-releasing peptides small enough to be synthesized by solid-phase methods will be biologically active and would be used.

Although the invention has been described with regard to its preferred embodiments, which constitute the best mode presently known to the inventors, it should be understood that various changes and modifications as would be obvious to one having the ordinary skill in this art may be made without departing from the scope of the invention. For example, the multi-step purification procedure, described herein, branches off from an inhibin purification procedure. It is expected that the desired product can be isolated using more direct procedures with fewer purification steps. Moreover, as is well known in the field of peptide hormones, shortening of a peptide chain may often be accomplished without adversely affecting the particular biological potency of interest; thus, shortening either or both chains of the dimer, even beyond deletion of the 15 residues at the C-terminus of the $\beta_B$ chain, may be possible. Dimers including such shortened chains are considered to be equivalent to those dimers hereinbefore disclosed.

Various features are emphasized in the following claims.

What is claimed is:

1. A method of treatment of a vertebrate animal so as to increase the secretion of FSH therein, which method comprises administering an effective amount of a protein which is a dimer of two polypeptide subunits linked together by disulfide bonding, each subunit having a formula selected from the formulae (a)

H—Gly—Leu—Glu—Cys—Asp—Gly—Lys—Val—Asn—Ile—
Cys—Cys—Lys—Lys—Gln—Phe—Phe—Val—Ser—Phe—Lys—
Asp—Ile—Gly—Trp—Asn—Asp—Trp—Ile—Ile—Ala—Pro—
Ser—Gly—Tyr—His—Ala—Asn—Tyr—Cys—Glu—Gly—Glu—
Cys—Pro—Ser—His—Ile—Ala—Gly—Thr—Ser—Gly—Ser—
Ser—Leu—Ser—Phe—His—Ser—Thr—Val—Ile—Asn—His—
Tyr—Arg—Met—Arg—Gly—His—Ser—Pro—Phe—Ala—Asn—
Leu—Lys—Ser—Cys—Cys—Val—Pro—Thr—Lys—Leu—Arg—
Pro—Met—Ser—Met—Leu—Tyr—Tyr—Asp—Asp—Gly—Gln—
Asn—Ile—Ile—Lys—Lys—Asp—Ile—Gln—Asn—Met—Ile—
Val—Glu—Glu—Cys—Gly—Cys—Ser—OH, or a naturally-occurring mammalian homolog thereof, and (b)

H—Gly—Leu—Glu—Cys—Asp—Gly—Arg—Thr—Asn—Leu—
Cys—Cys—Arg—Gln—Gln—Phe—Phe—Ile—Asp—Phe—Arg—
Leu—Ile—Gly—Trp—$R_{26}$—Asp—Trp—Ile—Ile—Ala—Pro—
Thr—Gly—Tyr—Tyr—Gly—Asn—Tyr—Cys—Glu—Gly—Ser—
Cys—Pro—Ala—Tyr—Leu—Ala—Gly—Val—Pro—Gly—Ser—
Ala—Ser—Ser—Phe—His—Thr—Ala—Val—Val—Asn—Gln—
Tyr—Arg—Met—Arg—Gly—Leu—Asn—Pro—Gly—Thr—Val—
Asn—Ser—Cys—Cys—Ile—Pro—Thr—Lys—Leu—Ser—Thr—
Met—Ser—Met—Leu—Tyr—Phe—Asp—Asp—Glu—Tyr—Asn—
Ile—Val—Lys—Arg—Asp—Val—Pro—Asn—Met—Ile—Val—
Glu—Glu—Cys—Gly—Cys—Ala—OH, wherein $R_{26}$ is Ser or Asn, or a naturally-occurring mammalian homolog thereof.

2. A method according to claim 1 wherein both of said subunits of said protein have the formula:

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH.

3. A method according to claim 1 wherein both of said subunits of said protein have the formula:

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—$R_{26}$—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—
Lys—Arg—Asp—Val—Pro—Asn—Met—Ile—Val—Glu—
Glu—Cys—Gly—Cys—Ala—OH, wherein $R_{26}$ is Ser or Asn.

4. A method of treatment according to claim 1 wherein said protein is a heterodimer in which one subunit has the formula:

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH and the other subunit has the formula:

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—$R_{26}$—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—
Lys—Arg—Asp—Val—Pro—Asn—Met—Ile—Val—Glu—
Glu—Cys—Gly—Cys—Ala—OH, wherein $R_{26}$ is Ser or Asn.

5. A method of treatment according to claim 1 wherein $R_{26}$ is Ser.

6. A method of treatment according to claim 3 wherein $R_{26}$ is Ser.

7. A method of treatment according to claim 4 wherein $R_{26}$ is Ser.

8. A method of treatment according to claim 1 wherein $R_{26}$ is Asn.

9. A method of treatment according to claim 3 wherein $R_{26}$ is Asn.

10. A method of treatment according to claim 4 wherein $R_{26}$ is Asn.

11. A pharmaceutical composition which comprises a pharmaceutically-acceptable carrier plus an amount, effective to cause an increase in fertility in a male or female vertebrate animal, of a substantially pure protein which is a homodimer or a heterodimer of two polypeptide subunits linked together by disulfide bonding, each subunit having a formula selected from the formulae:

(a) H—Gly—Leu—Glu—Cys—Asp—Gly—Lys—Val—Asn—
Ile—Cys—Cys—Lys—Lys—Gln—Phe—Phe—Val—Ser—
Phe—Lys—Asp—Ile—Gly—Trp—Asn—Asp—Trp—Ile—Ile—
Ala—Pro—Ser—Gly—Tyr—His—Ala—Asn—Tyr—Cys—
Glu—Gly—Glu—Cys—Pro—Ser—His—Ile—Ala—Gly—
Thr—Ser—Gly—Ser—Ser—Leu—Ser—Phe—His—Ser—
Thr—Val—Ile—Asn—His—Tyr—Arg—Met—Arg—Gly—
His—Ser—Pro—Phe—Ala—Asn—Leu—Lys—Ser—Cys—
Cys—Val—Pro—Thr—Lys—Leu—Arg—Pro—Met—Ser—
Met—Leu—Tyr—Tyr—Asp—Asp—Gly—Gln—Asn—Ile—
Ile—Lys—Lys—Asp—Ile—Gln—Asn—Met—Ile—Val—Glu—
Glu—Cys—Gly—Cys—Ser—OH, and (b) H—Gly—Leu—
Glu—Cys—Asp—Gly—Arg—Thr—Asn—Leu—Cys—Cys—
Arg—Gln—Gln—Phe—Phe—Ile—Asp—Phe—Arg—Leu—
Ile—Gly—Trp—$R_{26}$—Asp—Trp—Ile—Ile—Ala—Pro—Thr—
Gly—Tyr—Tyr—Gly—Asn—Tyr—Cys—Glu—Gly—Ser—
Cys—Pro—Ala—Tyr—Leu—Ala—Gly—Val—Pro—Gly—
Ser—Ala—Ser—Ser—Phe—His—Thr—Ala—Val—Val—
Asn—Gln—Tyr—Arg—Met—Arg—Gly—Leu—Asn—Pro—
Gly—Thr—Val—Asn—Ser—Cys—Cys—Ile—Pro—Thr—
Lys—Leu—Ser—Thr—Met—Ser—Met—Leu—Tyr—Phe—
Asp—Asp—Glu—Tyr—Asn—Ile—Val—Lys—Arg—Asp—
Val—Pro—Asn—Met—Ile—Val—Glu—Glu—Cys—Gly—

-continued
Cys—Ala—OH, wherein $R_{26}$ is Ser or Asn.

12. A pharmaceutical composition in accordance with claim 11 wherein said protein is a homodimer of two subunits having the same formula.

13. A pharmaceutical composition in accordance with claim 11 wherein said protein is a heterodimer wherein one subunit has the formula: (a)

H—Gly—Leu—Glu—Cys—Asp—Gly—Lys—Val—Asn—Ile—
Cys—Cys—Lys—Lys—Gln—Phe—Phe—Val—Ser—Phe—
Lys—Asp—Ile—Gly—Trp—Asn—Asp—Trp—Ile—Ile—Ala—
Pro—Ser—Gly—Tyr—His—Ala—Asn—Tyr—Cys—Glu—
Gly—Glu—Cys—Pro—Ser—His—Ile—Ala—Gly—Thr—
Ser—Gly—Ser—Ser—Leu—Ser—Phe—His—Ser—Thr—
Val—Ile—Asn—His—Tyr—Arg—Met—Arg—Gly—His—
Ser—Pro—Phe—Ala—Asn—Leu—Lys—Ser—Cys—Cys—
Val—Pro—Thr—Lys—Leu—Arg—Pro—Met—Ser—Met—
Leu—Tyr—Tyr—Asp—Asp—Gly—Gln—Asn—Ile—Ile—
Lys—Lys—Asp—Ile—Gln—Asn—Met—Ile—Val—Glu—
Glu—Cys—Gly—Cys—Ser—OH,

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—$R_{26}$—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—
Lys—Arg—Asp—Val—Pro—Asn—Met—Ile—Val—Glu—
Glu—Cys—Gly—Cys—Ala—OH, wherein $R_{26}$ is Ser or Asn.

14. A pharmaceutical composition in accordance with claim 11 wherein $R_{26}$ is Ser.

15. A pharmaceutical composition in accordance with claim 13 wherein $R_{26}$ is Ser.

16. A pharmaceutical composition in accordance with claim 1 wherein $R_{26}$ is Asn.

17. A pharmaceutical composition in accordance with claim 13 wherein $R_{26}$ is Asn.

18. A pharmaceutical composition in accordance with claim 12 wherein both of said subunits of said protein have the formula:

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—Ser—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—
Lys—Arg—Asp—Val—Pro—Asn—Met—Ile—Val—Glu—
Glu—Cys—Gly—Cys—Ala—OH.

19. A pharmaceutical composition in accordance with claim 12 wherein both of said subunits of said protein have the formula:

H—Gly—Leu—Glu—Cys—Asp—Gly—Arg—Thr—Asn—
Leu—Cys—Cys—Arg—Gln—Gln—Phe—Phe—Ile—Asp—
Phe—Arg—Leu—Ile—Gly—Trp—Asp—Trp—Ile—Ile—
Ala—Pro—Thr—Gly—Tyr—Tyr—Gly—Asn—Tyr—Cys—
Glu—Gly—Ser—Cys—Pro—Ala—Tyr—Leu—Ala—Gly—
Val—Pro—Gly—Ser—Ala—Ser—Ser—Phe—His—Thr—
Ala—Val—Val—Asn—Gln—Tyr—Arg—Met—Arg—Gly—
Leu—Asn—Pro—Gly—Thr—Val—Asn—Ser—Cys—Cys—
Ile—Pro—Thr—Lys—Leu—Ser—Thr—Met—Ser—Met—
Leu—Tyr—Phe—Asp—Asp—Glu—Tyr—Asn—Ile—Val—
Lys—Arg—Asp—Val—Pro—Asn—Met—Ile—Val—Glu—
Glu—Cys—Gly—Cys—Ala—OH.

* * * * *

UNITED STATES PATENT AND TRADEMARK OFFICE
CERTIFICATE OF CORRECTION

PATENT NO. : 4,973,577
DATED : November 27, 1990
INVENTOR(S) : Vale, et al.

It is certified that error appears in the above-identified patent and that said Letters Patent is hereby corrected as shown below:

Column 8, line 37, "Calig." should be --Calif.--.
Column 10, line 59, "Val Asn" should be --Val-Asn--.
Column 10, line 60, "Gyl-Trp Asn" should be --Gly-Trp-Asn--.
Column 10, line 63, "Arg Gln" should be --Arg-Gln--.
Column 10, line 64, "Trp-Ile-Ala-Pro." should be --Trp-Ile-Ile-Ala-Pro.--.
Column 10, line 65, "upom" should be --upon--.
Column 13, line 36, before "disclosures", insert --the--.
Column 17, lines 22-23, between the two formulae in Claim 13, insert --and the other subunit has the formula: (b)--.
Column 18, line 4, change "claim 1" to --claim 11--.
Column 18, line 28, change the third line of the sequence in Claim 19 to read --Phe-Arg-Leu-Ile-Gly-Trp-Asn-Asp-Trp-Ile-Ile--.

Signed and Sealed this

Seventh Day of July, 1992

Attest:

DOUGLAS B. COMER

Attesting Officer

Acting Commissioner of Patents and Trademarks